US011179310B2

(12) United States Patent
Prigge et al.

(10) Patent No.: US 11,179,310 B2
(45) Date of Patent: Nov. 23, 2021

(54) FRAGRANCE COMPOSITIONS AND PRODUCTS WITH MOOD ENHANCING EFFECTS

(71) Applicants: SYMRISE AG, Holzminden (DE); JOHNSON & JOHNSON CONSUMER INC., Skillman, NJ (US)

(72) Inventors: Katharine A. Prigge, West Caldwell, NJ (US); Kathleen Casey Pansini, Stanhope, NJ (US); Karen Solari Dugan, Leonia, NJ (US); Mansi Batra Patney, Secaucus, NJ (US); Keith McDermott, Bound Brook, NJ (US); Lena Quay Siew Huang, Bellewaters (SG); Dirk Braun, Cedar Grove, NJ (US); Cheong Ai Peng, Singapore (SG); Alejandra Sulbaran, Wanaque, NJ (US); Helene Zunino, Saint Cyr L'Ecole (FR); Kathryn Luedtke, Bellingham, MA (US); Devin Garcia, Middlesex, NJ (US); Kirsten Keynes, Princeton, NJ (US); Janeta Nikolovski, Princeton, NJ (US)

(73) Assignees: SYMRISE AG, Holzminden (DE); JOHNSON & JOHNSON CONSUMER INC., Skillman, NJ (US)

( * ) Notice: Subject to any disclaimer, the term of this patent is extended or adjusted under 35 U.S.C. 154(b) by 145 days.

(21) Appl. No.: 16/611,507

(22) PCT Filed: Apr. 26, 2018

(86) PCT No.: PCT/EP2018/060691
§ 371 (c)(1),
(2) Date: Nov. 7, 2019

(87) PCT Pub. No.: WO2018/206297
PCT Pub. Date: Nov. 15, 2018

(65) Prior Publication Data
US 2021/0077374 A1    Mar. 18, 2021

Related U.S. Application Data
(60) Provisional application No. 62/502,928, filed on May 8, 2017.

(51) Int. Cl.
| | |
|---|---|
| *A61Q 19/00* | (2006.01) |
| *A61Q 19/10* | (2006.01) |
| *A61K 8/49* | (2006.01) |
| *A61K 8/34* | (2006.01) |
| *A61K 8/37* | (2006.01) |
| *A61Q 13/00* | (2006.01) |

(52) U.S. Cl.
CPC .......... *A61K 8/4973* (2013.01); *A61K 8/342* (2013.01); *A61K 8/37* (2013.01); *A61K 8/498* (2013.01); *A61Q 13/00* (2013.01); *A61Q 19/00* (2013.01); *A61Q 19/10* (2013.01); *A61K 2800/5922* (2013.01)

(58) Field of Classification Search
CPC ........ A61Q 19/00; A61Q 13/00; A61K 8/498; A61K 8/4973; A61K 8/47; A61K 8/022; A61K 2800/5922
USPC .......................................................... 514/450
See application file for complete search history.

(56) References Cited

U.S. PATENT DOCUMENTS

2008/0096791 A1 * 4/2008 Behan .................... A61Q 13/00
512/27
2013/0172429 A1    7/2013 Hoelscher et al.

FOREIGN PATENT DOCUMENTS

WO    2006136828 A1    12/2006

OTHER PUBLICATIONS

International Search Report and Written Opinion dated Jul. 2, 2018 for corresponding PCT Application No. PCT/EP2018/060691.

\* cited by examiner

*Primary Examiner* — Yanzhi Zhang
(74) *Attorney, Agent, or Firm* — Polsinelli PC

(57) ABSTRACT

The present invention primarily relates to novel fragrance compositions suitable for enhancing the mood of a subject, preferably a human, novel products containing the same as well as novel uses and methods of such compositions and products.

17 Claims, 1 Drawing Sheet

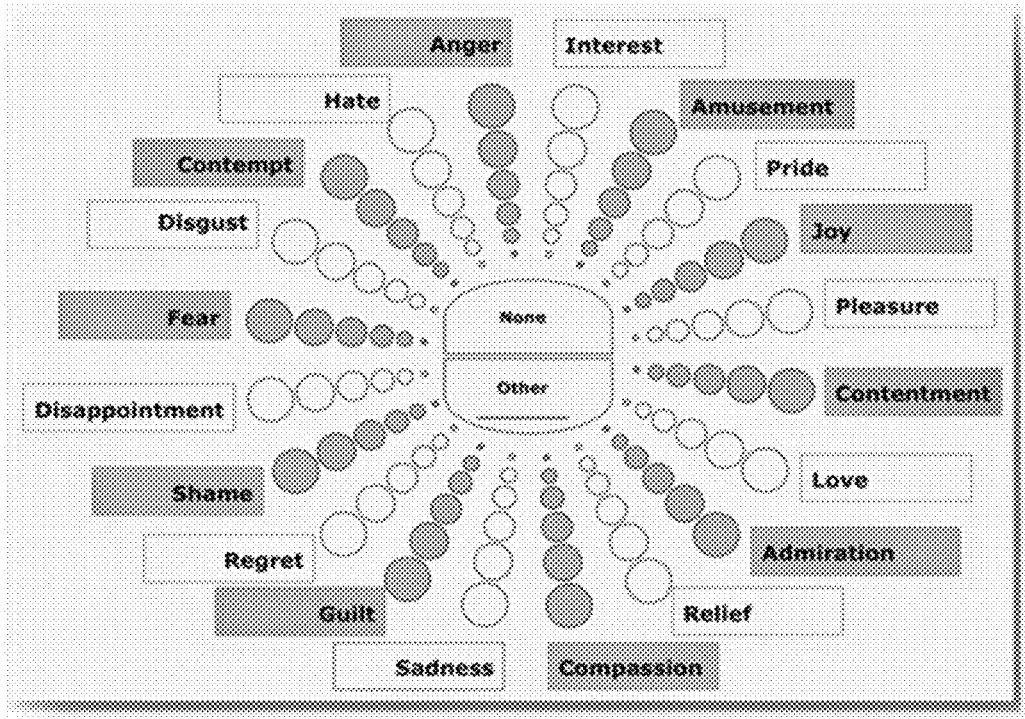
Emotional wheel - score sheet
INSTRUCTIONS:
Please select the emotion you felt while smelling the scent. You may choose more than one emotion.
Please indicate the intensity with which you experienced the emotion by filling in the appropriate circle (the bigger the circle, the stronger your emotional experience).

FRAGRANCE COMPOSITIONS AND PRODUCTS WITH MOOD ENHANCING EFFECTS

CROSS-REFERENCE TO RELATED APPLICATIONS

This application is a national stage application (under 35 U.S.C. § 371) of PCT/EP2018/060691, filed Apr. 26, 2018, which claims benefit of U.S. Provisional Application No. 62/502,928, filed May 8, 2017, which are incorporated herein by reference in their entireties.

FIELD OF INVENTION

The present invention primarily relates to novel fragrance compositions suitable for enhancing the mood of a subject, preferably a human, novel products containing the same as well as novel uses and methods of such compositions and products.

Further aspects of the present invention will arise from the description below, in particular from the examples, as well as from the attached patent claims.

STATE OF THE ART

Many current market products claim to have an "energizing" or "calming" benefit to the end user. Olfactory information is believed to be carried directly from the olfactory bulb into the limbic system, or the emotional heart of the brain. Therefore, scent plays a powerful role in evoking and reinforcing emotions and fragrance is the ideal vehicle to deliver positive mood enhancement to an individual. Aside from descriptions of aromatherapy, however, there are few cited reports that reveal how to design fragrance that are optimized both for hedonic acceptance and shown to deliver targeted emotional benefit.

In the context of the present invention, reference is made to prior art documents AU 2007200749 A1, BRPI0700678A, CA 2579562 A1, CN 101028237 A, EP 1829559 A1, JP 2007238610 A and US 20070207220 A1, all relating to methods for improving sleep behaviours. Furthermore, reference is made to US 20080096790 A1 relating to fragrance compositions with beneficial effects, US 20100174586 A1 relating to methods for measuring emotive response and selection preference to visual stimuli, US 20040033279 relating to a process for effecting the relaxation of muscles of a human by means of a fragrance, EP 2158895 B1 relating to a method for energizing human beings, U.S. Pat. No. 6,830,755 B2 relating to a method for relaxing human beings using personal care compositions, U.S. Pat. No. 8,435,572 B2 relating to compositions and methods for promoting a relaxation state, EP 1293554 A1 relating to stress relieving perfumes and stress relieving perfume compositions containing the same, and WO 2002049600 A1 relating to perfume compositions which aim to promote relaxed and related mood states in subjects.

Methods for reducing stress or eliciting a calming effect on humans often rely on the application of complex essential oils directly to the skin (cf. U.S. Pat. No. 8,435,572 B2) which may contain allergens and/or skin sensitizers.

BRIEF DESCRIPTION OF DRAWINGS

The Figure shows an Emotional Wheel, which is a semi-semantic, theoretically derived, and empirically tested mechanism to measure emotional reactions to objects, events, and situations.

DESCRIPTION OF THE INVENTION

The present invention demonstrates that a fragrance formulation designed with minimal use of essential oils (which is preferred according to one embodiment of the present invention) can still elicit an emotional response.

In addition, previous attempts have required the application of a product or fragrance oils directly to the skin, requiring touch or massage, which confounds the effects of measuring the olfactive benefits of fragrance alone (cf. US 20070207220 A1). In addition, previous attempts require a multi-step product/sensory regime (cf. US 20070207220 A1). This study, however, isolates the benefit of fragrance via olfactive analysis of a fragrance when formulated in a typical consumer product.

Prior approaches rely heavily on measuring stress reduction via the assessment of salivary cortisol levels (cf. US 20080096790). However, cortisol is an indirect measure of stress as cortisol is involved in a number of neurological events and levels can vary greatly between individuals. To account for the high inter-subject variation, cortisol sampling typically requires an artificial stress induction protocol to induce stress and measure the return of cortisol levels in a baseline in a laboratory setting (e.g. a Stroop test). The testing methods underlying the present invention, in contrast, directly assess the positive, subconscious, emotional response of the respondent's face and vocal expression to determine the ability of fragrance to provide an enhanced emotional experience (cf. example 3 below). The testing does not impose stress on the respondent and more directly mimics real life interaction with the fragrance and consumer product.

While previous attempts measure the level of excitation or energizing effect (cf. EP 2158895 B1), few fragrances have been evaluated for their direct effect to elicit a specific mood-boosting benefit in the form of a positive emotion (e.g., happiness and joy).

Untrained individuals often cannot tell (due to lack of ability or vocabulary) or will not tell how they really feel about a product, especially when they are receiving compensation for testing or evaluation. Therefore relying heavily on interviews, questionnaires, or self-assessment psychometric tools to measure true human emotion is problematic. In these experiments, we performed a holistic psychological and behavioural analysis to determine the mood-altering effects of fragrance. As humans have evolved as highly social creatures, individuals spontaneously and subconsciously communicate through verbal and facial responses. Evaluation of these facial and voice responses, in response to a fragrance stimuli, allows for the subconscious and unaltered evaluation of human emotion in response to scent.

Typically, prior art evaluations of the emotional response to fragrance are often limited in scope to a single testing location (e.g., US 2008/0096790 in the UK). However, it is known that cultural differences exist in fragrance evaluation, and these differences may severely alter and influence the emotional associations and response to a scent. In the experiments underlying the present invention the inventors captured the effect of cultural variation on fragrance evaluation by assessing the emotional associations to the tested fragrances in 6 different countries: US, UK, Philippines, Egypt, China and India. The results demonstrate that it is possible to formulate fragrances that show universal emotion enhancing benefits across unique and distinct cultures.

Furthermore, while the underlying study shows that not all pleasant fragrances are equally sufficient in eliciting a positive emotional response on the end user, the present invention demonstrates that it is feasible to design fragrances with desirable emotional benefits using the rules (cf. features of the attached claims) and tests (cf. example 3) described herein. It was a primary object of the present invention to provide novel and beneficial fragrance compositions and products suitable for enhancing the mood of a subject. Moreover, it was an object of the present invention to provide different, beneficial uses of such compositions and, respectively, products and corresponding methods.

Further objects underlying the present invention follow from the description below and the attached patent claims.

According to a first aspect of the present invention, the stated objects are achieved by a fragrance composition consisting of or comprising

- a) two or more compounds of group (A) in a total amount of between 5 and 25 wt.-%, preferably between 10 and 20 wt.-%, group (A) consisting of compounds with a musk odor impression, a molecular mass between 235 g/mol and 270 g/mol and a LOG KOW value of at least 3.0, preferably between 3.0 and 5.8,
- b) two or more, preferably four or more compounds of group (B) in a total amount of between 1 and 25 wt.-%, preferably between 5 and 15 wt.-%, group (B) consisting of compounds with a woody odor impression, a molecular mass between 208 g/mol and 236 g/mol and a LOG KOW value of at least 3.3, preferably between 3.3 and 5.2,
- c) two or more, preferably three or more compounds of group (C) in a total amount of between 0.5 and 5 wt.-%, preferably between 1 and 2.5 wt.-%, group (C) consisting of lactones with a fruity odor impression, a molecular mass between 170 g/mol and 198 g/mol and a LOG KOW value of at least 2.5, preferably between 2.5 and 3.6,
- d) two or more, preferably three or more compounds of group (D) in a total amount of between 15 and 35 wt.-%, preferably between 20 and 30 wt.-%, group (D) consisting of esters with a floral, fresh and/or green odor impression, a molecular mass between 150 g/mol and 226 g/mol and a LOG KOW value of at least 2.0, preferably between 2.0 and 4.9,
- e) two or more, preferably three or more compounds of group (E) in a total amount of between 1 and 5 wt.-%, preferably between 1.3 and 2.5 wt.-%, group (E) consisting of ketones with 2,6,6-Trimethylcyclohex(di)enylbutenone structure, with a floral and/or fruity odor impression, a molecular mass between 190 g/mol and 192 g/mol and a LOG KOW value of at least 2.5, preferably between 2.5 and 4.5,
- f) two or more, preferably five or more compounds of group (F) in a total amount of between 1 and 30 wt.-%, preferably between 5 and 30 wt.-%, group (F) consisting of esters with a floral and/or fruity odor impression, a molecular mass between 116 g/mol and 275 g/mol and a LOG KOW value of at least 0.2, preferably 1.3, preferably between 0.2 or 1.3 and 4.6,
- g) two or more, preferably three or more compounds of group (G) in a total amount of between 0.1 and 15 wt.-%, preferably between 0.5 and 10 wt.-%, group (G) consisting of aldehydes with a fresh, green, floral and/or fruity odor impression, a molecular mass between 138 g/mol and 192 g/mol and a LOG KOW value of at least 1.1, preferably between 1.1 and 4.8,
- h) two or more, preferably four or more compounds of group (H) in a total amount of between 10 and 30 wt.-%, preferably between 15 and 25 wt.-%, group (H) consisting of alcohols with a fresh, green, floral and/or fruity odor impression, a molecular mass between 100 g/mol and 178 g/mol and a LOG KOW value of at least 0.3, preferably between 0.3 and 3.9, and
- i) dipropylene glycol (DPG) and/or one or more other solvents, preferably DPG, in a total amount of between 1 and 30 wt.-%, preferably between 1 and 20 wt.-%, more preferably between 1 and 10 wt.-%, in each case based on the total weight (100 wt.-%) of the composition.

Preferably, the fragrance composition additionally comprises or consists of

- j) one or more compounds of group (J) in a total amount of between 0.1 and 20 wt.-%, preferably between 2 and 5 wt.-%, group (J) consisting of Magnolan ((2R,4R,4aS,9bR)-2,4-dimethyl-4,4a,5,9b-tetrahydroindeno[1,2-d][1,3]dioxine), Florhydral (3-(3-isopropylphenyl)butanal), Benzaldehyde, Anisaldehyde (4-methoxybenzaldehyde), Ethylvanillin (3-ethoxy-4-hydroxy-benzaldehyde), Methylbenzoate, Cumarin (chromen-2-one), Octahydrocumarin (3,4,4a,5,6,7,8,8a-octahydrochromen-2-one), Limonen (4-isopropenyl-1-methyl-cyclohexene), Jasmon (3-methyl-2-[(Z)-pent-2-enyl]cyclopent-2-en-1-one), Linalool (3,7-dimethylocta-1,6-dien-3-ol) and Veloutone (2,2,5-trimethyl-5-pentyl-cyclopentanone), based on the total weight (100 wt.-%) of the composition.

Furthermore, a fragrance composition according to the present invention, wherein one, two, more or all compounds of group (A) is/are selected from the group consisting of Ambrettolide, Ethylenbrassylat, Globalide®, Muscenone and Macrolide® Supra, preferably Ethylenbrassylat and Globalide®, and/or wherein one, two, more or all compounds of group (B) is/are selected from the group consisting of Isobomylcyclohexanol, Sandranol®, Ambroxide, Ebanol, Iso E Super and Sandalore, preferably Ambroxide, Isobornylcyclohexanol, Sandranol® and Ebanol, and/or wherein one, two, more or all compounds of group (C) is/are selected from the group consisting of Aldehyde C14 so called, Decalactone and Dodecalactone, preferably Aldehyde C14 so called, gamma Decalactone and delta Dodecalactone, and/or wherein one, two, more or all compounds of group (D) is/are selected from the group consisting of Hedione, Dimethylbenzylcarbinylbutyrate, cis-3-Hexenylsalicylate, Cyclohexylsalicylate, Benzylacetate, Herbaflorate, Leafovert® and Herbylpropionate, preferably Hedione, Dimethylbenzylcarbinylbutyrate and cis-3-Hexenylsalicylate, and/or wherein one, two, more or all compounds of group (E) is/are selected from the group consisting of Ionone, Damascone and Damascenone, preferably beta-Ionone, Delta-Damascone and Damascenone, and/or wherein one, two, more or all compounds of group (F) is/are selected from the group consisting of Ethylisobutyrate, Methylanthranilate, Sultanene®, Agrumex, Manzanate, Allylhepylate, Ethylmethylbutyrate, Cyclogalbanate®, Phenirat®, Citronellylacetate, Isoamylacetate, Prenylacetate, Isoamylbutyrate, Hexylacetate, Allylcyclohexylpropionate, Jasmaprunate, especially preferred Agrumex, Manzanate, Allylhepylate, Ethylmethylbutyrate and Cyclogalbanate®, and/or wherein one, two, more or all compounds of group (G) is/are selected from the group consisting of Florazone, Heliotropin/Piperonal, Vertocitral/Ligustral, Helional, Cyclamenaldehyde, Aldehyde C12, Melonal®, Citral FF, especially preferred Heliotropin/Piperonal, Vertocitral/Ligustral and Florazone, and/or wherein one, two, more or all compounds of group (H) is/are selected from the group consisting of Tetrahydrolinalool, Ethylmaltol, Florosa/Pyranol, Phenylethyldimethylcarbinol, Phenylethylalcohol, Ethyllinalool, Phenoxanol, Dihydromycrenol, cis-3-Hexenol, especially preferred Tetrahydrolinalool, Ethylmaltol, Florosa/Pyranol and Phenylethyldimethylcarbinol, is particularly advantageous and thus preferred.

According to a preferred embodiment of the present invention, the solvent or, respectively, one or more or all solvents contained in the fragrance composition according to the invention is/are selected from the group consisting of DPG, Isopropylmyristate (IPM), Ethanol (EtOH) and Triethylcitrate (TEC).

According to one embodiment, the fragrance composition according to the present invention comprises a total amount of less than 55 different substances, preferably less than 38.

The present invention is based on extensive testing of fragrances using psychological and behavioural parameters to classify the fragrances for the purpose of the present invention (cf. testing procedures described in example 3), namely fragrances that induce in subjects exposed to them positive moods and emotions, particularly "joy and happiness".

When following the features of the attached claims and the herein described embodiments of compositions according to the invention as well as the testing procedures described herein (cf. example 3), a skilled person can easily provide a plurality of different fragrance compositions according to the invention.

A second aspect of the present invention relates to perfumed products comprising a fragrance composition according to the invention. Preferably, the term "perfumed" has to be understood such that the fragrance composition is contained in a sensorially effective amount (however, the products according to the invention may optionally comprise one or more further sensorially effective ingredients). Preferably the fragrance composition is contained in an amount sufficient to enhance the mood of a subject, preferably a human, more preferably wherein the fragrance composition is contained in a total amount in the range of from 0.1 to 1 wt.-%, preferably from 0.2 to 0.7 wt.-%, more preferably from 0.3 to 0.5 wt.-%.

The term "effective amount" refers to the amount of the fragrance composition which is needed to create the desired response in a human of the desired age, for example, two months to three years old, two months to eighteen months, and two months to twelve months. Most importantly, the user must be able to perceive the odor of the fragrance when administering the fragrance experience according to its typical usage instructions. Preferably, the fragrance composition will be used at a concentration as described above.

In connection with the present invention, "mood enhancing" effects are preferably determined according to one or more, preferably all, testing procedures described in example 3 below. Accordingly, "mood enhancing" effects are preferably selected from the ones described in example 3 below.

Preferably, a product according to the present invention is selected from the group consisting of personal cosmetic, toiletry, and healthcare products such as dry and wet wipes, washes, baths, shampoos, gels, soaps, mousses, cleansing compositions, bath oils, other bath compositions that may be added to a bath, other wash compositions that may be used directly on the skin, leave-on personal care products include personal cosmetic, toiletry, and healthcare products such as sticks, balms, mousses, sprays, lotions, creams, gels, powders, oils, waxes, perfumes, other personal care compositions that may be applied to the skin and not rinsed off, or home or laundry care products such as fabric detergents, fabric softeners, linen sprays, air care products, diffusers, devices or other products that may be used in the home for the purpose of cleaning surfaces, fabrics or perfuming the air.

Both cleansing and leave-on personal care products are particularly useful in delivering the fragrances of the present invention. For example, a fragrance composition may be produced by blending the selected fragrance ingredients under ambient conditions until the final mixture is homogenous using equipment and methodology commonly known in the art. It is preferable to store the final fragrance mixture (composition) under ambient conditions for a few hours after mixing before using it as a component of e.g. a cleansing or leave-on personal care product. In order to improve the solubilization of the fragrance composition in aqueous personal care products, the sensory fragrance may be pre-blended with one or more of the nonionic surfactants.

Suitable cleansing personal care products include personal cosmetic, toiletry, and healthcare products such as dry and wet wipes, washes, baths, shampoos, gels, soaps, mousses, cleansing compositions, bath oils, other bath compositions that may be added to a bath, or other wash compositions that may be used directly on the skin. Any formulation useful for the above and which is compatible with the fragrance compositions is suitable for use in the present invention. In order to achieve the desired response in an infant mammal, the cleansing personal care product may be used in a dosing amount that is in accordance with the prescribed directions of the cleansing personal care product.

Suitable leave-on personal care products include personal cosmetic, toiletry, and healthcare products such as sticks, balms, mousses, sprays, lotions, creams, gels, powders, oils, waxes, perfumes, or other personal care compositions that may be applied to the skin and not rinsed off. Any formulation useful for the above and which is compatible with the fragrance composition is suitable for use in the present invention. Methods for preparing suitable leave-on personal care products are well known to those skilled in the art of preparing personal care products. In order to achieve the desired response in an infant mammal, the leave-on personal care product may be used in a dosing amount that is in accordance with the prescribed directions of the cleansing personal care product.

Compositions containing the fragrance composition and which are capable of delivering the fragrance experience may also include, but are not limited to, wipes, washes, baths, shampoos, gels, soaps, sticks, balms, sachets, pillows, mousses, sprays, lotions, creams, cleansing compositions, oils, bath oils, aerosols, and substances which may be used with vaporizers.

Products according to the present invention have been shown to be particularly useful in the context of the present invention as they increase the amount of time the user is willing to spend using the product which enhances the benefit. This is beneficial when the user of the product is a mom with her baby as increased length of bathing experiences provides more touch, eye contact, contact, etc. which has been shown elsewhere to be beneficial for both infant development and maternal well being.

Preferably, a product according to the invention, in particular a personal care product according to the invention additionally contains cotton powder. Surprisingly, it has been discovered that cotton containing personal care products when used in combination with the fragrance compositions of the present invent are particularly beneficial in enhancing the mood and emotion of the user. Such products have been shown to be particularly useful in increasing the amount of time the user is willing to spend using the product (cf. above). Preferably the cotton powder will be used in a total amount in the range of from 0.1 to 10 wt. %, preferably 0.25 to 6 wt. %, more preferably 0.5 to 3 wt. %, based on the total weight of the product. In some aspects, the personal care product additionally containing cotton powder is preferably a cleansing wash.

A further aspect of the present invention relates to the use of a fragrance composition according to the present invention as mood enhancing composition or as mood enhancing ingredient, preferably in a product according to the invention, in particular for enhancing the mood of a human.

Accordingly, the present invention also relates to the use of a product according to the invention as mood enhancing product, in particular for enhancing the mood of a human.

The present invention also relates to a method for enhancing the mood of a subject, preferably of a human, consisting of or comprising the following steps:
(i) providing a fragrance composition according to the present invention or a product according to the present invention, and
(ii) contacting the fragrance composition/product with the subject, preferably a human, in an amount sufficient to enhance the mood of the subject/human.

Preferably, the fragrance composition is contained in a product selected from the group consisting of the following products or, respectively, wherein the product is selected from the group consisting of the following products: personal cosmetic, toiletry, and healthcare products such as dry and wet wipes, washes, baths, shampoos, gels, soaps, mousses, cleansing compositions, bath oils, other bath compositions that may be added to a bath, other wash compositions that may be used directly on the skin, leave-on personal care products include personal cosmetic, toiletry, and healthcare products such as sticks, balms, mousses, sprays, lotions, creams, gels, powders, oils, waxes, perfumes, other personal care compositions that may be applied to the skin and not rinsed off, or home or laundry care products such as fabric detergents, fabric softeners, linen sprays, air care products, diffusers, devices or other products that may be used in the home for the purpose of cleaning surfaces, fabrics or perfuming the air.

Further preferred embodiments of uses and methods of the present invention become apparent in light of the above description, in particular regarding preferred embodiments of compositions and products according to the present invention.

The invention will now be described in more detail hereinafter with references to selected examples.

EXAMPLES

Example 1: Fragrance Composition According to the Invention

Fragrance A (fragrance composition according to the invention) is prepared by mixing the following ingredients at the indicated weight percentages (wt. %).

TABLE 1

| Fragrance A | parts in weight |
| --- | --- |
| AGRUMEX LC | 2.75% |
| ALDEHYDE C14 SO-CALLED | 1.47% |
| ALLYL CYCLOHEXYL PROPIONATE | 0.29% |
| ALLYL HEPTOATE | 1.96% |
| AMBRETTOLIDE | 0.25% |
| AMBROXIDE 10% IPM | 0.88% |
| ANISIC ALDEHYDE PURE 10% DPG | 0.98% |
| BENZYL ACETATE | 1.86% |
| COUMARIN 10% DPG | 2.94% |
| CYCLAMEN ALDEHYDE | 2.16% |
| CYCLOGALBANAT ® | 0.10% |
| CYCLOHEXYL SALICYLATE | 0.20% |
| DAMASCONE DELTA | 0.10% |
| DECALACTONE GAMMA | 0.98% |
| DIHYDRO MYRCENOL | 2.35% |
| DIMETHYL BENZYL CARBINYL BUTYRATE | 0.59% |
| DODECALACTONE DELTA | 0.20% |
| EBANOL | 0.29% |
| ETHYL LINALOOL | 5.78% |
| ETHYL MALTOL 10% DPG | 0.78% |
| ETHYL METHYL BUTYRATE-2 | 0.69% |
| ETHYL VANILLIN | 0.59% |
| ETHYLENE BRASSYLATE | 8.33% |
| FLORAZON | 0.10% |
| FLORHYDRAL | 0.39% |
| GLOBALIDE ® | 4.31% |
| HEDIONE | 18.14% |
| HELIONAL | 4.36% |
| HELIOTROPIN | 0.69% |
| HERBYL PROPIONATE | 0.39% |
| HEXENOL CIS-3 | 0.29% |
| HEXENYL ACETATE CIS-3 | 0.25% |
| HEXENYL SALICYLATE CIS-3 | 2.16% |
| HEXYL ACETATE | 0.98% |
| IONONE BETA | 1.37% |
| ISO E SUPER | 1.47% |
| ISOAMYL ACETATE | 0.05% |
| ISOAMYL BUTYRATE | 0.10% |
| JASMAPRUNAT | 0.88% |
| JASMONE CIS | 0.10% |
| LIGUSTRAL | 0.49% |
| MACROLIDE ® SUPRA | 3.24% |
| MELONAL ® 10% DPG | 0.20% |
| METHYL ANTHRANILATE 1% DPG | 1.18% |
| METHYL BENZOATE 10% DPG | 0.29% |
| MUSCENONE | 0.29% |
| OCTAHYDRO COUMARIN | 0.20% |
| ORANGE OIL 15X COLORLESS | 0.29% |
| PHENIRAT ® | 2.45% |
| PHENOXANOL | 4.90% |
| PHENYLETHYL ALCOHOL BA FREE | 4.41% |
| PRENYL ACETATE | 0.49% |
| SANDALORE | 4.41% |
| TETRAHYDRO LINALOOL | 4.61% |

Example 2: Application Examples

Wash Formulation:

A wash formulation for personal care purposes was made as follows in Table 2

TABLE 2

Product Formulation

| Ingredients | parts in wt. % |
|---|---|
| Fragrance composition (example 1) | 0.35% |
| other ingredients of unfragranced gentle cleansing product | 99.65% |

Lotion:

A lotion for personal care purposes was made as follows in Table 3

TABLE 3

Product Formulation

| Ingredients | parts in wt. % |
|---|---|
| Fragrance composition (example 1) | 0.35% |
| other usual lotion ingredients | 99.65% |

Oil Formulation:

An oil formulation for personal care purposes was made as follows in Table 4

TABLE 4

Product Formulation

| Ingredients | parts in wt. % |
|---|---|
| Fragrance composition (example 1) | 0.4% |
| other usual oil formulation ingredients | 99.6% |

Powder Formulation:

A powder for personal care purposes formulation was made as follows in Table 5

TABLE 5

Product Formulation

| Ingredients | parts in wt. % |
|---|---|
| Fragrance composition (example 1) | 0.2% |
| other usual powder formulation ingredients | 99.8% |

It is apparent that the fragrance compositions of the present invention can be used in a wide variety of products. Suitable products include, but are not limited to personal care products, bath products and body washes, skin care products, lotions, powders, gels, mousses, sprays, foams, hair care products including shampoos, conditioners and sprays. Preferred products according to the present invention are described in the general part of the specification above.

Example 3—Test Procedures

A plurality of different fragrance compositions were tested on a group of 40 healthy, female subjects between the ages of 18-34 years old with at least one child 0-6 months in order to assess the mood enhancing effect of the fragrance compositions.

Subjects with known acute or chronic illness, pregnancy, smokers or known anosmia or hyponosmia were omitted from the study. Participants were briefed on the purpose and description of the global procedure prior to testing.

Subjects were placed in a testing room and positioned in front of a video camera. Fragrance compositions comprising of different fragrance formulations were presented in a fully balanced and rotated manner. During evaluation, the respective composition was administered to the respondent's gloved hands and she was instructed to evaluate the product's scent as she mixed the product in 2 L of warm water (40° C.). The subject's facial expressions, prosody (tone and emotion of speech), verbatim verbal response to prompted questions, and subjective assessment of emotion (written emotional questionnaire) were captured. Each subject was allowed a one minute rest between different fragrance compositions or, respectively, products.

The behavioural analysis was performed by assessing the facial expressions and voice of the respondent during and immediately following fragrance exposure. Facial coding was performed using the Facial Action Coding System (FACS v.2002). Prosody (voice analysis) was extracted from the amplitude (dB), mean fundamental frequency (i.e. pitch) and coefficient of variation of the fundamental frequency (i.e. musicality) of the subject's voice when prompted to describe any images, feelings or emotions the scent brings to mind. The subject's level of arousal (engagement) was calculated from the level of intensity of facial expressions and vocal amplitude. Valence (pleasantness) was determined from the polarity of the facial expression and variability of vocal pitch.

This emotional mapping analysis revealed that fragrance compositions according to the present invention (e.g. Fragrance A according to example 1) as well as products containing the same provided a significantly more pleasant (positive valence) and significantly higher level of engagement (arousal) than other compositions (i.e. fragrance compositions outside the scope of the claims), demonstrating that a fragrance composition according to the present invention elicits a positive mood-enhancing benefit.

TABLE 6

Averaged Emotional Mapping Results

| Fragrance comp. | Valence | Arousal |
|---|---|---|
| Fragrance A | 19.63* | 5.73* |
| Fragrance B** | 14.49 | 4.09 |

*P < 0.05, N = 40

**Fragrance B: exemplary comparative example (i.e. fragrance composition outside the scope of the claims)

Verbal analysis was performed from the verbatim responses of subjects' to a question after smelling the scented product. Each respondent was prompted "What do you think about this scent? Can you describe what images, feelings or emotions it brings to mind?" The verbal analysis compared the number of distinct terms mentioned in regards to each fragrance as compared to the total number of terms spoken (total word count). Respondents more frequently spoke of the emotions/terms of happy, joy, laugh, smile, play and fun in reference to fragrance compositions according to the invention, e.g. Fragrance A, as compared to e.g. Fragrance B. The results for smile were significantly higher (P<0.05).

TABLE 7

Verbatim Verbal Analysis of Responses

| Target Word | Happy | Joy | Laugh | Smile | Play | Fun |
|---|---|---|---|---|---|---|
| Word Count | 157 | 20 | 12 | 19 | 20 | 14 |
| (% of Total) | 1% | 0.10% | 0.04% | 0.10% | 0.10% | 0.07% |

TABLE 7-continued

Verbatim Verbal Analysis of Responses

| Target Word | Happy | Joy | Laugh | Smile | Play | Fun |
|---|---|---|---|---|---|---|
| Fragrance A | 17% | 20% | 17% | 42%* | 10% | 29% |
| Fragrance B | 16% | 10% | 10% | 11% | 5% | 0% |

*P < 0.05, N = 40

The Emotional Wheel (see The Figure) is a semi-semantic, theoretically derived, and empirically tested mechanism to measure emotional reactions to objects, events, and situations. Based on Scherer's Component Process Model (Scherer, 2005), the tool is designed to measure emotional reactions to objects, events, and situations, which makes it easy to be applied to various scenarios, including the measurement of emotions elicited by consumer products. The 20 emotion families are arranged in a circular pattern with the axes defined by two major dimensions of emotional space. The respondent is asked to indicate the emotion(s) she experienced while choosing the intensity (1-5) for a single emotion or blend of several of the 20 distinct emotions on the wheel. The five degrees of intensity are presented, represented by different sized circles.

The Emotional Wheel responses of the 40 subjects were averaged and both, fragrance compositions according to the invention (e.g. Fragrance A) and comparative examples (e.g. Fragrance B), were assessed regarding their capability to elicit positive emotions via self-assessment. Fragrance compositions according to the invention (e.g. Fragrance A) were found to be significantly better at eliciting stronger positive emotions of joy, pleasure, love, relief and compassion than comparative examples (e.g. Fragrance B).

TABLE 8

Averaged Emotional Wheel Responses

| | Fragrance A | Fragrance B |
|---|---|---|
| Interest | 1.7 | 1.2 |
| Pride | 1.3 | 0.9 |
| Joy* | 3.1 | 2.1 |
| Pleasure* | 3.1 | 2.4 |
| Contentment | 2.3 | 1.7 |
| Love* | 2.7 | 2.3 |
| Admiration | 1.5 | 0.6 |
| Relief* | 1.4 | 1.1 |
| Compassion* | 1.3 | 0.9 |
| Sadness | 0.1 | 0.5 |

*P < 0.05, N = 40

Implicit Association Testing (IAT) is a well-established and validated psychometric tool used in psychological and consumer research that reveals a respondent's perceptions by gauging his/her timed reactions to stimuli (e.g., fragrance, images or words). The IAT is a computer based test that is easily scalable and allows for the global evaluation of a fragrance relative to specific product attributes or emotions. The IAT measures are based on response latencies for two tasks that differ in instructions for using two response keys to classify categories of stimuli.

In this test, implicit associations were determined from the responses of 50 female respondents between the ages of 18-34 with at least one biological child age 0-6 months living at home in each of the following countries: UK, Philippines, India, Egypt and China. The fragranced product was first diluted in warm water and presented for sniff evaluation in a 2 oz. wide mouth jar.

The results revealed variable levels of consumers' associations and perception of each fragrance to target concept words (e.g., joyful and cheerful). Academic calculations for associations (D scores; Greenwald, Nosek & Benaji, 2003) were used to determine the level of association to the attributes. The results are summarized within each country and are assigned a value of 1, 2 or 3 corresponding to an association of low, medium or high for each attribute, respectively. Fragrance compositions according to the invention (e.g. Fragrance A) showed significantly stronger associations to the positive emotions of joyful, cheerful and happy than comparative examples (e.g. Fragrance B).

TABLE 9

Implicit Association Testing (IAT) Results

| | Joyful | |
|---|---|---|
| | Fragrance A | Fragrance B |
| UK | 3 | 2 |
| Philippines | 3 | 2 |
| India | 3 | 2 |
| Egypt | 3 | 2 |
| China | 3 | 2 |

| | Cheerful | |
|---|---|---|
| | Fragrance A | Fragrance B |
| UK | 3 | 2 |
| Philippines | 3 | 2 |
| India | 3 | 2 |
| Egypt | 2 | 1 |
| China | 3 | 2 |

The invention claimed is:

1. A fragrance composition comprising:
   a) two or more compounds of group (A) in a total amount of between 5 and 25 wt.-%, wherein the compounds of group (A) are compounds with a musk odor impression, a molecular mass between 235 g/mol and 270 g/mol, and a LOG KOW value of at least 3.0, and wherein one or more compounds of group (A) is/are chosen from ambrettolide, ethylenbrassylat, (3E)-oxacyclohexadec-3-en-2-one, muscenone, and 16-oxacyclohexadecan-1-one;
   b) two or more compounds of group (B) in a total amount of between 1 and 25 wt.-%, wherein the compounds of group (B) are compounds with a woody odor impression, a molecular mass between 208 g/mol and 236 g/mol, and a LOG KOW value of at least 3.3, and wherein one or more compounds of group (B) is/are chosen from isobornylcyclohexanol, (E)-2-ethyl-4-(2,2,3-trimethyl-1-cyclopent-3-enyl)but-2-en-1-ol, ambroxide, ebanol, tetramethyl acetyloctahydronaphthalenes, and sandalore;
   c) two or more compounds of group (C) in a total amount of between 0.5 and 5 wt.-%, wherein the compounds of group (C) are lactones with a fruity odor impression, a molecular mass between 170 g/mol and 198 g/mol, and a LOG KOW value of at least 2.5, and wherein one or more compounds of group (C) is/are chosen from gamma-undecalactone, decalactone, and dodecalactone;
   d) two or more compounds of group (D) in a total amount of between 15 and 35 wt.-%, wherein the compounds of group (D) are esters with a floral, fresh and/or green odor impression, a molecular mass between 150 g/mol and 226 g/mol, and a LOG KOW value of at least 2.0, and wherein one or more compounds of group (D) is/are chosen from hedion, dimethylbenzylcarbinylbutyrate, cis-3-hexenylsalicylate, cyclohexylsalicylate, benzylacetate, herbaflorate, (Z)-3-hexen-1-yl methyl carbonate, and herbylpropionate;

e) two or more compounds of group (E) in a total amount of between 1 and 5 wt.-%, wherein the compounds of group (E) are ketones with 2,6,6-trimethylcyclohex(di) enylbutenone structure, with a floral and/or fruity odor impression, a molecular mass between 190 g/mol and 192 g/mol, and a LOG KOW value of at least 2.5, and wherein one or more compounds of group (E) is/are chosen from ionon, damascene, and damascenone;

f) two or more compounds of group (F) in a total amount of between 1 and 30 wt.-%, wherein the compounds of group (F) are esters with a floral and/or fruity odor impression, a molecular mass between 116 g/mol and 275 g/mol, and a LOG KOW value of at least 0.2, and wherein one or more compounds of group (F) is/are chosen from ethylisobutyrate, methylanthranilate, ethyl-2-cyclopentenyl acetate, agrumex, manzanate, allylhepylate, ethylmethylbutyrate, galbanum oxyacetate, phenoxyethyl isobutyrate, citronellylacetate, isoamylacetate, prenylacetate, isoamylbutyrate, hexylacetate, allylcyclohexylpropionate, and jasmaprunate;

g) two or more compounds of group (G) in a total amount of between 0.1 and 15 wt.-%, wherein the compounds of group (G) are aldehydes with a fresh, green, floral and/or fruity odor impression, a molecular mass between 138 g/mol and 192 g/mol, and a LOG KOW value of at least 1.1, and wherein one or more compounds of Group (G) is/are chosen from florazone, heliotropin/piperonal, vertocitral/ligustral, helional, cyclamenaldehyde, aldehyde C12, melon heptenal, citral FF, heliotropin/piperonal, vertocitral/ligustral, and florazone;

h) two or more compounds of group (H) in a total amount of between 10 and 30 wt.-%, wherein the compounds of group (H) are alcohols with a fresh, green, floral and/or fruity odor impression, a molecular mass between 100 g/mol and 178 g/mol, and a LOG KOW value of at least 0.3, and wherein one or more compounds of Group (H) is/are chosen from tetrahydrolinalool, ethylmaltol, florosa/pyranol, phenylethyldimethylcarbinol, phenylethylalcohol, ethyllinalool, phenoxanol, dihydromycrenol, and cis-3-hexenol; and i) a solvent selected from Dipropylene glycol (DPG), isopropyl myristate, ethanol, triethyl citrate or combination thereof.

2. The fragrance composition according to claim 1, wherein the composition additionally comprises:

j) one or more compounds of group (J) in a total amount of between 0.1 and 20 wt.-%, wherein the compounds of group (J) are Magnolan ((2R,4R,4aS,9bR)-2,4-dimethyl-4,4a,5,9b-tetrahydroindeno[1,2-d][1,3]dioxine), Florhydral (3-(3-isopropylphenyl)butanal), Benzaldehyde, Anisaldehyde (4-methoxybenzaldehyde), Ethylvanillin (3-ethoxy-4-hydroxy-benzaldehyde), Methylbenzoate, Cumarin (chromen-2-one), Octahydrocumarin (3,4,4a,5,6,7,8,8a-octahydrochromen-2-one), Limonen (4-isopropenyl-1-methylcyclohexene), Jasmon (3-methyl-2-[(Z)-pent-2-enyl] cyclopent-2-en-1-one), Linalool (3,7-dimethylocta-1,6-dien-3-ol) and Veloutone (2,2,5-trimethyl-5-pentylcyclopentanone), based on the total weight (100 wt.-%) of the composition.

3. The fragrance composition according to claim 1, wherein the composition comprises less than 55 different substances.

4. A perfumed product comprising a fragrance composition according to claim 1.

5. The product according to claim 4 comprising a sensorially effective amount of the fragrance composition.

6. The product according to claim 4, wherein the product is selected from the group consisting of personal cosmetic, toiletry, and healthcare products, dry and wet wipes, washes, baths, shampoos, gels, soaps, mousses, cleansing compositions, bath oils, other bath compositions that may be added to a bath, other wash compositions that may be used directly on the skin, leave-on personal care products include personal cosmetic, toiletry, and healthcare products, sticks, balms, mousses, sprays, lotions, creams, gels, powders, oils, waxes, perfumes, other personal care compositions that may be applied to the skin and not rinsed off, or home or laundry care products, fabric detergents, fabric softeners, linen sprays, air care products, diffusers, devices or other products that may be used in the home for the purpose of cleaning surfaces, fabrics or perfuming the air.

7. The product according to claim 4, further comprising cotton powder.

8. The fragrance composition according to claim 1 comprising:
b) four or more compounds of group (B) in a total amount of between 5 and 15 wt.-%.

9. The fragrance composition according to claim 1 comprising:
c) three or more compounds of group (C) in a total amount of between 0.1 and 2.5 wt.-%.

10. The fragrance composition according to claim 1 comprising:
d) three or more compounds of group (D) in a total amount of between 20 and 30 wt.-%.

11. The fragrance composition according to claim 1 comprising:
e) three or more compounds of group (E) in a total amount of between 1.3 and 2.5 wt.-%.

12. The fragrance composition according to claim 1 comprising:
f) five or more compounds of group (F) in a total amount of between 5 and 30 wt.-%.

13. The fragrance composition according to claim 1 comprising:
g) three or more compounds of group (G) in a total amount of between 0.5 and 10 wt.-%.

14. The fragrance composition according to claim 1 comprising:
h) four or more compounds of group (H) in a total amount of between 15 and 25 wt.-%.

15. The fragrance composition according to claim 1 comprising:
i) dipropylene glycol in a total amount of between 1 and 20 wt.-%.

16. A method for enhancing the mood of a subject comprising:
providing a fragrance composition according to claim 1 or a product comprising the fragrance composition, and
(ii) bringing an amount of the fragrance composition or product comprising the fragrance composition into contact with the subject, wherein the amount is sufficient to enhance the mood of the subject.

17. The method according to claim 16, wherein the product is selected from the group consisting of the following products: personal cosmetic, toiletry, and healthcare products, dry and wet wipes, washes, baths, shampoos, gels, soaps, mousses, cleansing compositions, bath oils, other bath compositions that may be added to a bath, other wash compositions that may be used directly on the skin, leave-on personal care products include personal cosmetic, and healthcare products, sticks, balms, mousses, sprays, lotions, creams, gels, powders, oils, waxes, perfumes, other personal care compositions that may be applied to the skin and not rinsed off, or home or laundry care products, fabric detergents, fabric softeners, linen sprays, air care products, diffusers, devices or other products that may be used in the home for the purpose of cleaning surfaces, fabrics or perfuming the air.

* * * * *